(12) United States Patent
Milo (10) Patent No.: US 10,548,584 B2
(45) Date of Patent: Feb. 4, 2020

(54) MOUTH GAG

(71) Applicant: Milo Medical IP, LLC, Akron, OH (US)

(72) Inventor: Anton G. C. Milo, Akron, OH (US)

(73) Assignee: Milo Medical IP, LLC, Akron, OH (US)

(*) Notice: Subject to any disclaimer, the term of this patent is extended or adjusted under 35 U.S.C. 154(b) by 193 days.

(21) Appl. No.: 15/715,516

(22) Filed: Sep. 26, 2017

(65) Prior Publication Data

US 2018/0085106 A1   Mar. 29, 2018

Related U.S. Application Data

(60) Provisional application No. 62/400,147, filed on Sep. 27, 2016.

(51) Int. Cl.
*A61B 17/02* (2006.01)

(52) U.S. Cl.
CPC ................ *A61B 17/0206* (2013.01)

(58) Field of Classification Search
CPC ...... A61B 13/00; A61B 17/02; A61B 17/0206
USPC ................................. 606/237–241
See application file for complete search history.

(56) References Cited

U.S. PATENT DOCUMENTS

| | | | | |
|---|---|---|---|---|
| 1,137,585 A | * | 4/1915 | Craig, Jr. ........... | A61O 5/90 433/140 |
| 1,388,421 A | * | 8/1921 | Forgrave ............ | A61B 1/24 600/239 |
| 2,697,432 A | * | 12/1954 | Scinta ............... | A61B 1/24 600/239 |
| 2,756,742 A | * | 7/1956 | Barton .............. | A61B 1/24 128/200.26 |
| 2,947,305 A | * | 8/1960 | Storz ............... | A61B 1/24 600/239 |
| 4,024,859 A | * | 5/1977 | Slepyan ............ | A61B 1/24 600/215 |
| 4,064,873 A | * | 12/1977 | Swenson ........... | A61B 1/24 600/215 |
| 4,151,837 A | * | 5/1979 | Millard, Jr. ........ | A61B 1/24 600/215 |
| 4,213,451 A | * | 7/1980 | Swenson ........... | A61B 1/24 600/215 |

(Continued)

FOREIGN PATENT DOCUMENTS

| WO | 2006054301 | 5/2006 |
|---|---|---|
| WO | 2015081008 | 6/2015 |
| WO | WO-2017051039 A1 * | 3/2017 |

OTHER PUBLICATIONS

International Search Report and Written Opinion in International Application No. PCT/US2017/053402 dated Dec. 6, 2017.

*Primary Examiner* — Eric S Gibson
(74) *Attorney, Agent, or Firm* — Calfee, Halter & Griswold LLP (57) ABSTRACT

Mouth gags having a tongue blade that includes a spine and an engagement portion for engaging a tongue of a patient are disclosed herein. The spine has a front, a back, a first side and a second side. A plurality of ratchet notches are located on the first side and a plurality of ratchet notches located on the second side. The mouth gag also includes a ratchet mechanism. The ratchet mechanism has a plurality of ratchet teeth for engaging the ratchet notches and a plurality of release tabs for disengaging the ratchet teeth from the ratchet notches.

20 Claims, 7 Drawing Sheets

(56) References Cited

U.S. PATENT DOCUMENTS

| | | | | |
|---|---|---|---|---|
| 6,254,591 | B1 | 7/2001 | Roberson | |
| 6,558,392 | B1* | 5/2003 | Martini | A61B 17/025 |
| | | | | 433/140 |
| 6,921,401 | B2* | 7/2005 | Lerch | A61B 17/688 |
| | | | | 606/232 |
| 7,887,483 | B2* | 2/2011 | Rosenberg | A61B 90/14 |
| | | | | 600/223 |
| 8,197,402 | B1* | 6/2012 | Cedeno | A61B 1/24 |
| | | | | 600/194 |
| 8,852,169 | B2* | 10/2014 | Milo | A61C 17/08 |
| | | | | 604/540 |
| 8,869,800 | B2* | 10/2014 | Allphin | A61M 16/0495 |
| | | | | 128/859 |
| 9,034,020 | B2* | 5/2015 | Knopfle | A61B 17/688 |
| | | | | 606/282 |
| 9,827,024 | B2* | 11/2017 | Cormier | A61B 17/8863 |
| 2012/0015317 | A1* | 1/2012 | Milo | A61C 17/08 |
| | | | | 433/29 |
| 2013/0220345 | A1 | 8/2013 | Allphin et al. | |
| 2014/0180298 | A1* | 6/2014 | Stevenson | A61B 17/7082 |
| | | | | 606/104 |
| 2015/0087918 | A1* | 3/2015 | Vasan | A61B 13/00 |
| | | | | 600/213 |
| 2016/0287224 | A1* | 10/2016 | Castro | A61B 13/00 |
| 2018/0085106 | A1* | 3/2018 | Milo | A61B 13/00 |
| 2018/0264507 | A1* | 9/2018 | Hiemer | A61M 3/0262 |

* cited by examiner

MOUTH GAG

RELATED APPLICATIONS

This application claims priority to and the benefits of U.S. Provisional Patent Application Ser. No. 62/400,147 filed on Sep. 27, 2016 and titled MOUTH GAG, which is incorporated herein by reference in its entirety.

TECHNICAL FIELD

The present invention relates generally to mouth gags and more particularly to a universal mouth gag that is configurable.

BACKGROUND OF THE INVENTION

Mouth gags, such as McIvor mouth gags, Dingman mouth gag, and Crowe Davis mouth gag are known in the art. Each mouth gag has a specific purpose and each is used for different procedures. A surgeon that performs all of the different procedures generally needs to purchase each of these expensive devices. In addition, each of these mouth gags need to be sterilized between uses. These mouth gags connect to a tongue blade such as, for example, the tongue blade shown and described in U.S. Pat. No. 8,852,169, which is incorporated herein by reference in its entirety.

SUMMARY

Exemplary mouth gags are disclosed herein. An exemplary mouth gag includes a tongue blade having a spine and an engagement portion for engaging a tongue of a patient. The spine has a front, a back, a first side and a second side. A plurality of ratchet notches are located on the first side and a plurality of ratchet notches located on the second side. The mouth gag also includes a ratchet mechanism. The ratchet mechanism has a plurality of ratchet teeth for engaging the ratchet notches and a plurality of release tabs for disengaging the ratchet teeth from the ratchet notches.

In this way, simple, universal and economical mouth gags are provided.

BRIEF DESCRIPTION OF THE DRAWINGS

These and other features and advantages of the present invention will become better understood with regard to the following description and accompanying drawings in which:

FIGS. 2B, 2C, and 2D;

FIG. 4 is a tongue blade having ratchet notches on the sides of the spine of FIG. 4 with an integrated suction tube, wherein the suction tube connects the tongue blade to the spine and provides the support there between;

DETAILED DESCRIPTION

Figure 1:
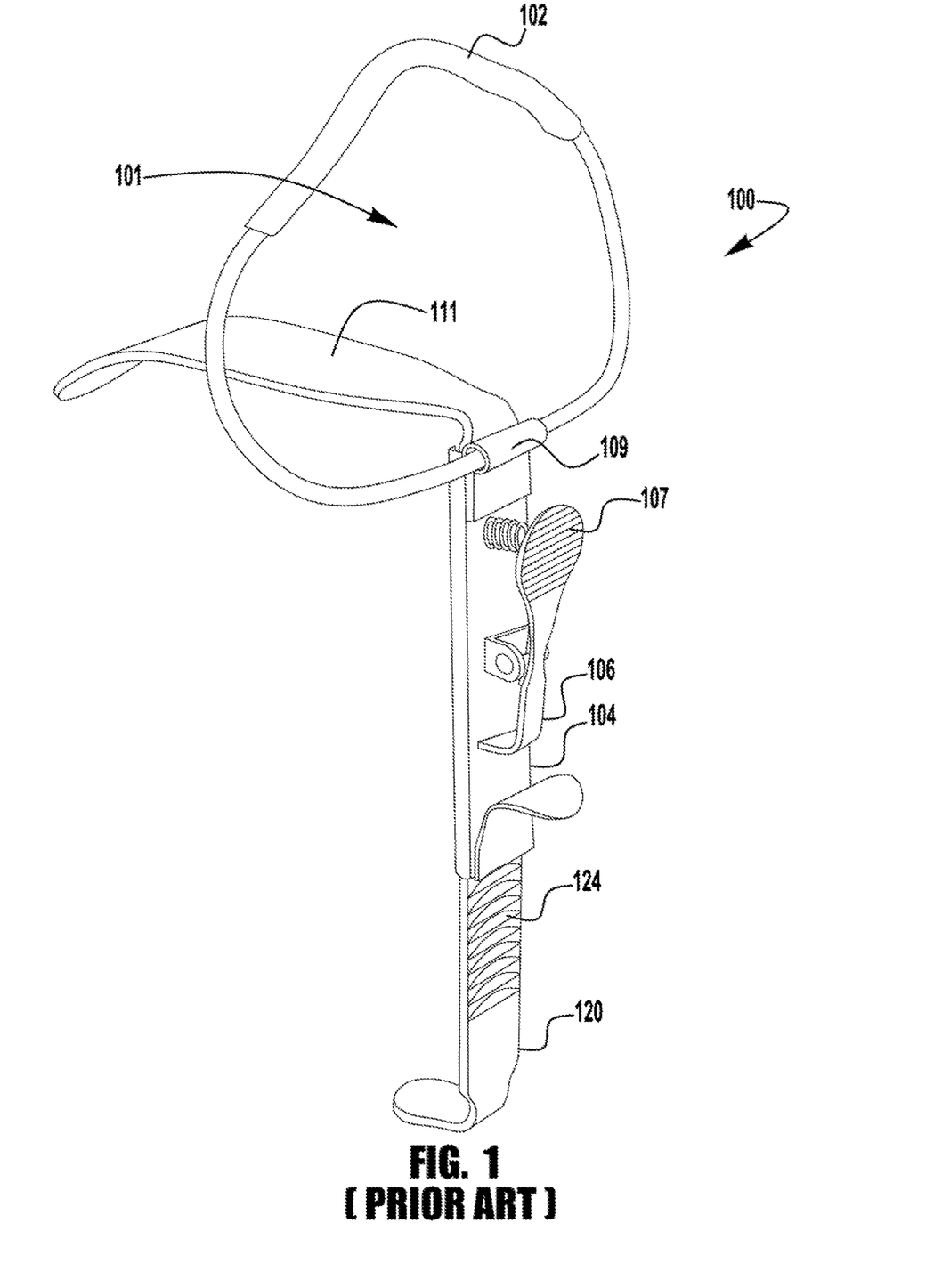
FIG. 1 is a prior art mouth gag.

FIG. 1 is a prior art McIvor mouth gag 100. Mouth gag 100 includes channel 104 that goes around a spine 120 of a tongue blade 111 and allow mouth gag 100 to slide up and down. Thumb lever 107 is used to release ratcheting mechanism 106 that engages with notches 124 in the spine 120 of the tongue blade 111 to adjust the amount a mouth is held open. Mouth gag 100 includes a rail 102 that forms an opening 101 through which medical instruments may be inserted during an operation. Rail 102 connects to rail holder 109 which is attached to channel 104. The top of rail 102 contacts a surface of the patient's upper jaw or teeth and the tongue blade 111 contacts the tongue or lower jaw. The surgeon slides the mouth gag 100 upward. Ratcheting mechanism 106, which is spring loaded in a downward position, slides upwards and engages the notches 124 in the spine, which prevents downward movement of mouth gag 100. Notches 124 are located on the front of the spine 120. When the procedure is complete, the surgeon pushes thumb release mechanism 107 which disengages ratcheting mechanism 106 and allows the mouth gag 100 to slide downward and be removed.

Figures 2, 2D:
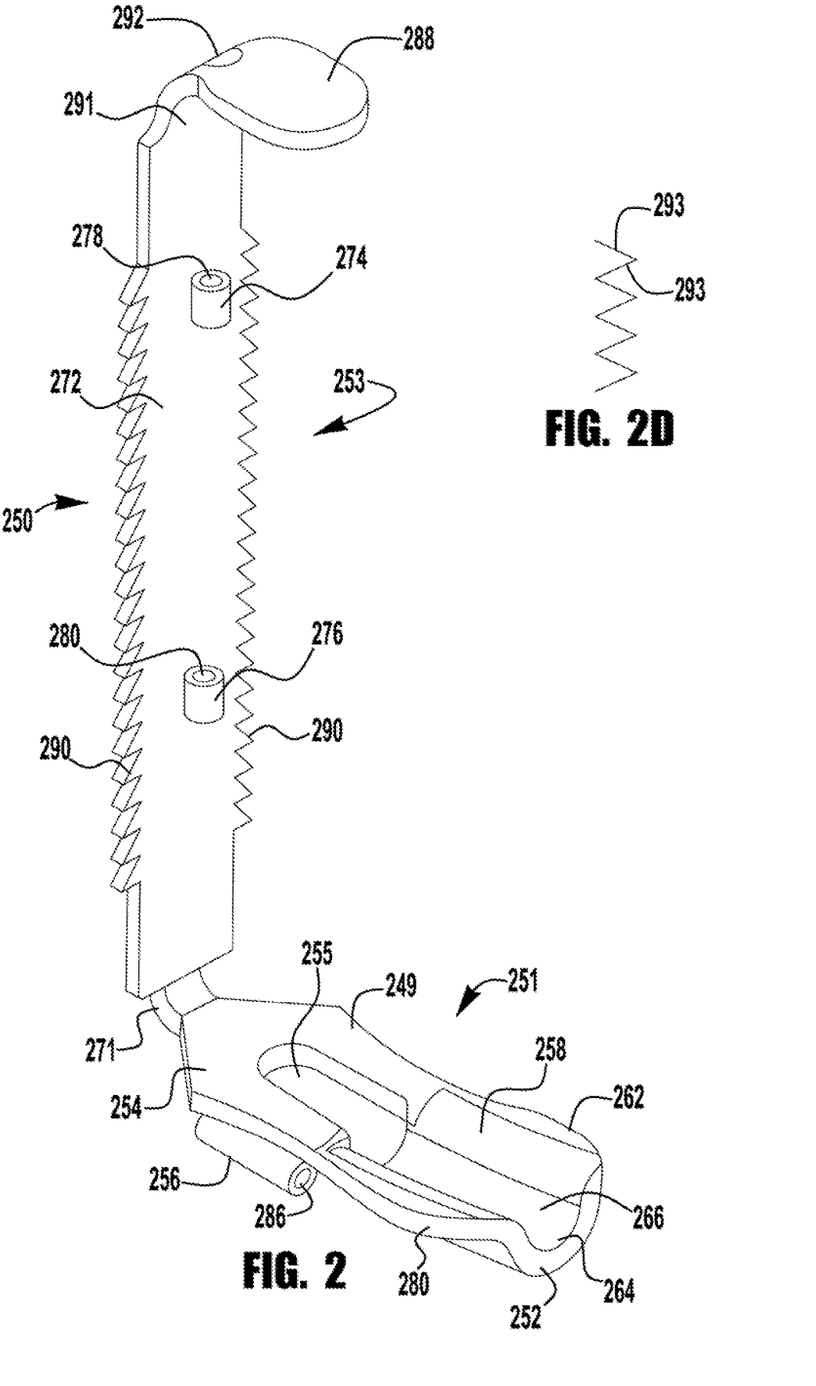
FIG. 2 is a prospective view of a tongue blade having ratchet notches on the sides of the spine.
Figure 2A:
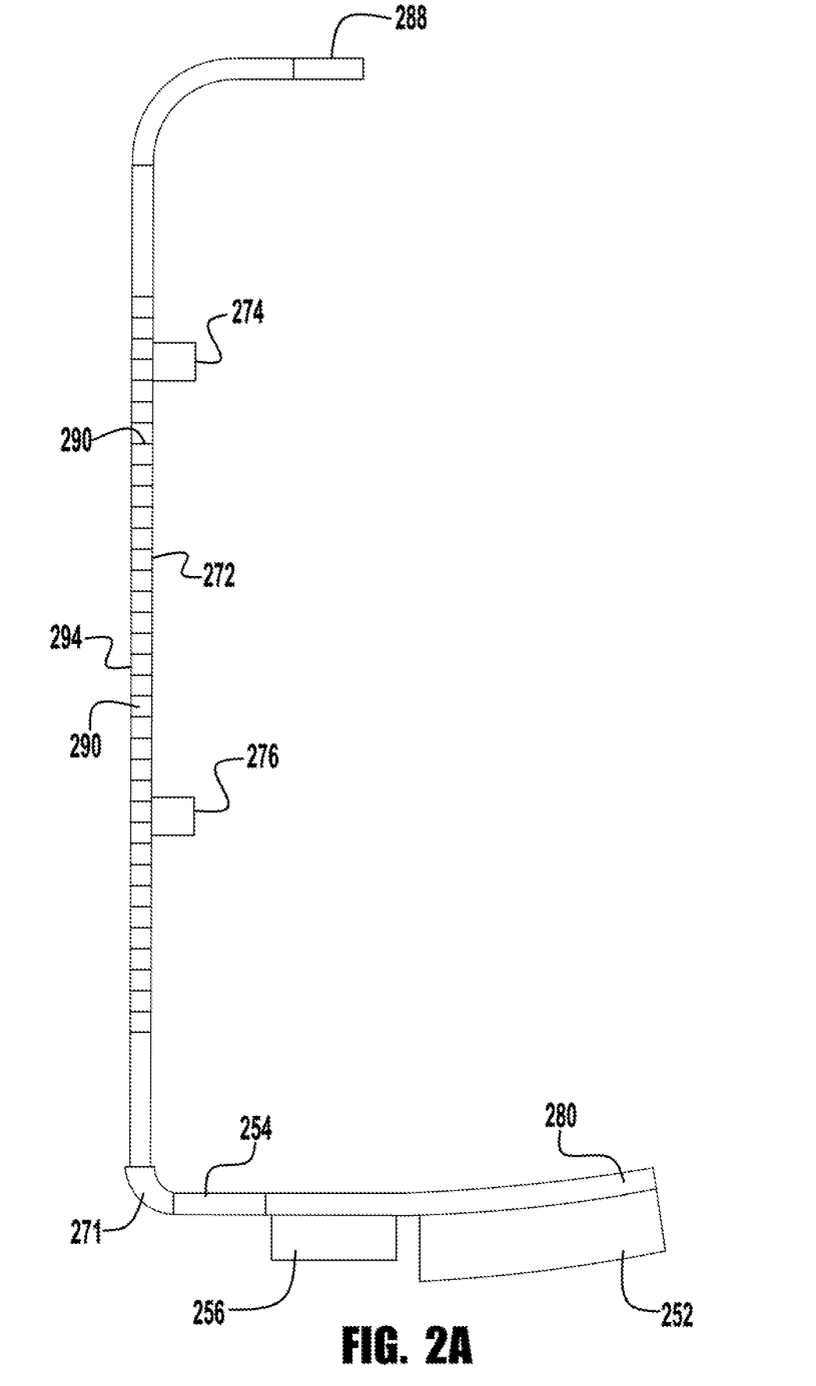
FIG. 2A is a side view of the tongue blade having ratchet notches on the sides of the spine of FIG. 2.
Figure 3:
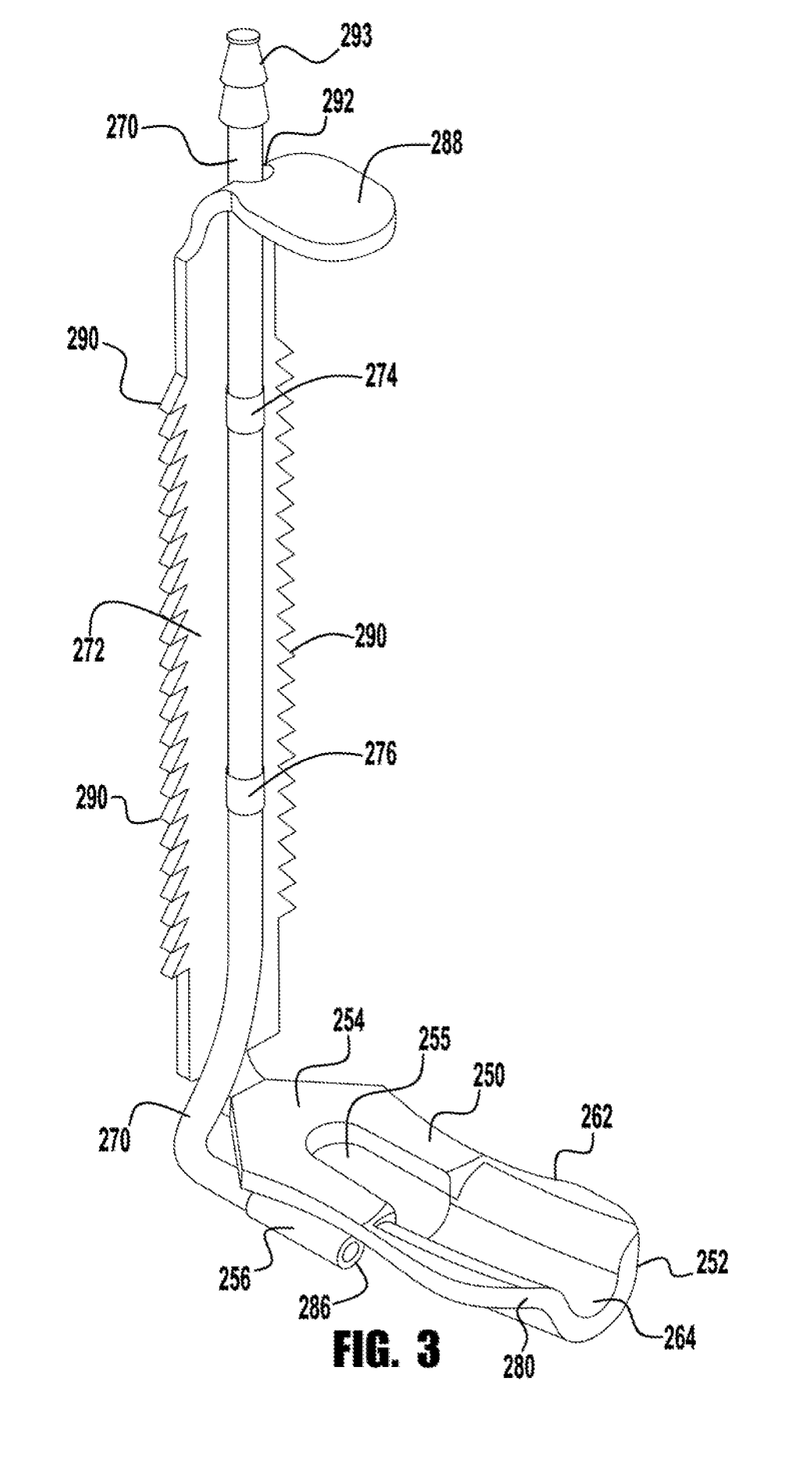
FIG. 3 is a tongue blade having ratchet notches on the sides of the spine of FIG. 2 with a suction tube connected thereto.

FIGS. 2, 2A and 3 illustrate exemplary embodiments of a novel tongue blade device 250. The tongue blade device 250 includes a first portion which is a tongue blade 251 for holding down a tongue and a second portion referred to herein as a spine 253. The tongue blade 251 has a distal end 252 for inserting into a patient's mouth during a surgical procedure and a proximal end 254 having a hollow tube (not shown) receiving member 256 and attached to spine 253 via a curved connector portion 271. A substantially U-shaped opening 255 is formed near end 254. The tongue blade 251 has a curved or rounded shape body 258 which acts as a tongue depressor and rests on the patient's tongue during a procedure. The exemplary distal end 252 has a fork or U-shaped appearance formed by two protrusions or walls 260, 262 extending therefrom which form a rounded or curved channel 264 having an opening 266. Walls 260, 262 curve upwardly as seen in FIG. 2A. A hollow disposable suction tube 270 (FIG. 3) is connected to the spine 272 and is in fluid communication with hollow connector or receiving member 256. The spine 272 has a pair of cylindrical shaped members 274, 276 having openings 278, 280 formed therein for receiving the tube 270 therein. Further, in the embodiment illustrated in FIG. 2, the suction tube receiving outlet member 256 has an opening 286 located adjacent to the proximal end 254 of the blade for removing noxious fumes, smoke, vaporized tissue, plumes generated by electrocautery and other debris from a patient's mouth during use in surgery. Spine 272 also has a wall 288 extending from end 291 which has an opening 292 therethrough for receiving tube 270. In some embodiments, wall 288 is bent at approximately 90 degrees or so with respect to spine 272.

Along each of the sides of spine 272 are a plurality of ratchet notches 290. Ratchet notches 290 may have a number of shapes. In some embodiments, the notches 290 are shaped so that the teeth 506 of ratchet mechanism 500 (FIG. 5) are able to slide upward on the spine without squeezing in release arms 510. In such an embodiment, the surgeon need only slide the ratcheting mechanism 500 upward to hold open the mouth open and the ratcheting mechanism 500, and in particular the teeth 506 of the ratcheting mechanism 500 prevent the ratcheting mechanism 500 from moving downward allowing the mouth to close without releasing the ratcheting mechanism. This operation is similar to a "zip tie" operation. When the surgeon is done with the procedure, the surgeon squeezes release arms 510 inward which causes teeth 506 to move outward and disengage from the ratchet notches 290.

Figure 2B:
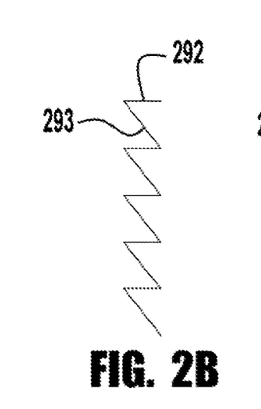
Figure 2C:
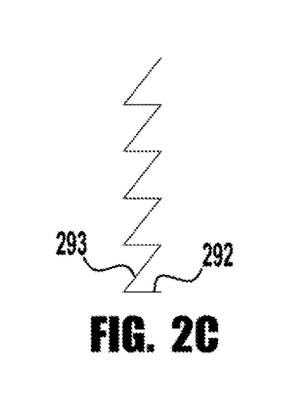

In some embodiments, the ratchet notches 290 have a flat surface 292 located in the orientation shown in FIG. 2B (if the portion that contacts the tongue is at the bottom of the page) and a sloped portion 293. In some embodiments, the ratchet notches 290 have a flat surface 292 located in the orientation shown in FIG. 2C (if the portion that contacts the tongue is at the bottom of the page) and a sloped portion 293. In some embodiments, the ratchet notches 290 have all sloped portions 293 as shown in FIG. 2D. In some embodiments, the release mechanism has to be released for movement in any direction.

When in use, smoke, plumes generated by electrocautery, noxious fumes and vaporized tissue removal is effectuated by attaching barb or connector 293 (FIG. 3) to a pneumatic device typical of the art which causes a suction effect from the tongue blade.

While the surgical application is taking place, the suction tube 270 in the patient's mouth and removing smoke, fumes, plumes generated by electrocautery, and vaporized tissue via opening (not shown, however it is similar to opening 101 in FIG. 1). The tongue blade 250, which is connected to the tube, is in the patient's mouth controlling the patient's tongue, thus preventing it from obstructing the application and removing smoke and vaporized tissue at the same time. The tongue blade suction tube 270 meanwhile evacuates the smoke, fumes, plumes generated by electrocautery, and vaporized tissue by sucking it through the receiving port or opening 286, through tube 270, and out through the pneumatic or other suction causing device (not shown) attached to barb 293. After use, the suction tube 270 can be removed and discarded. The spine 272 can be sanitized and reused with a new suction tube.

Figure 4:
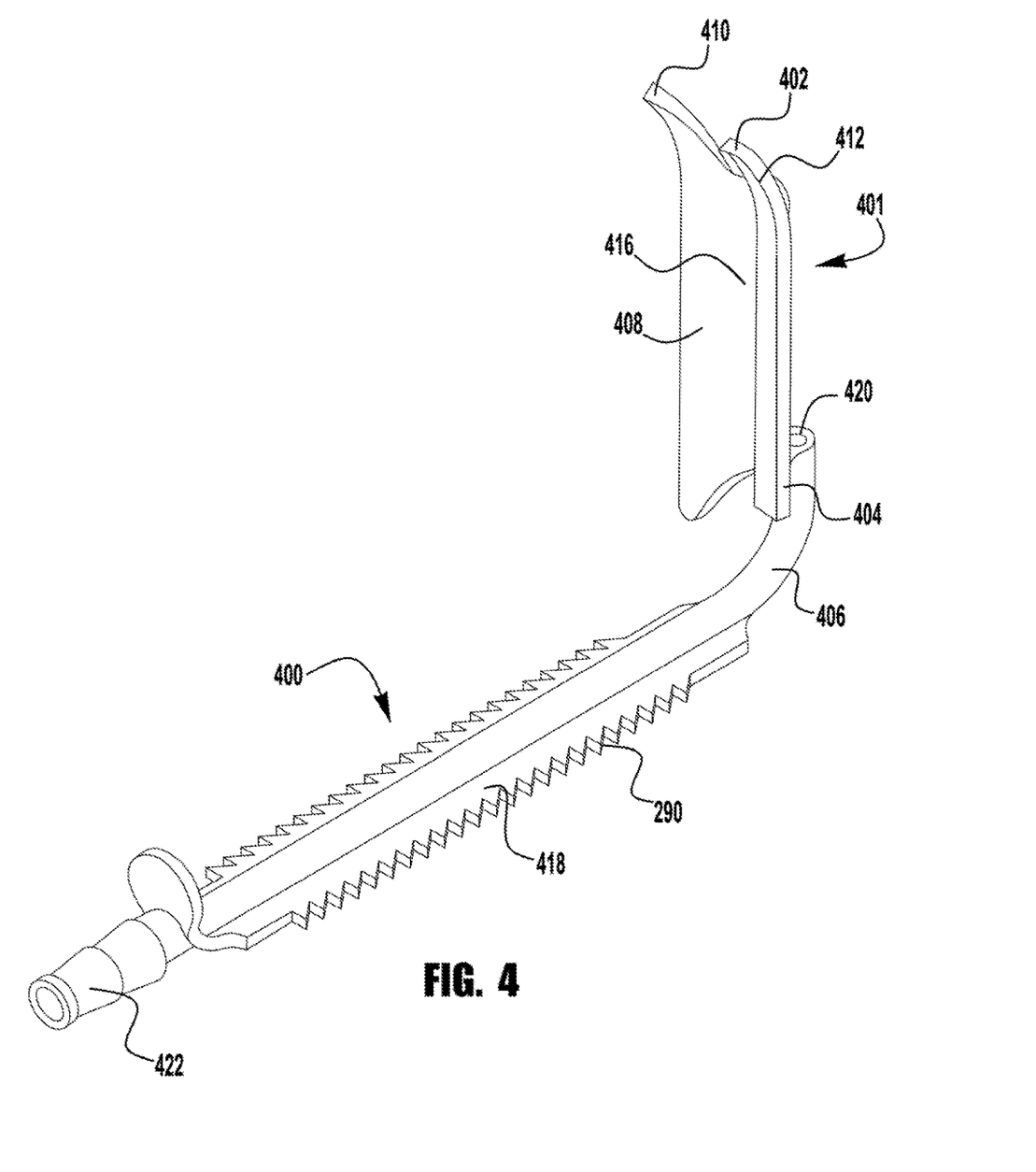

Another variation of the disclosure is a one-piece unit which is fabricated from a plastic, one or more polymers, a high impact plastic, thermoplastic, or the like. In some embodiments, the one-piece unit which is fabricated from one or more metals, a composite, or the like. In some embodiments, the on-piece unit is formed on a three-dimensional printer. FIG. 4 illustrates an exemplary embodiment of a one-piece tongue blade device 400 with integrated suction device 406 which can be disposable and fabricated of thermoplastic, the materials identified above, or any other suitable material. The tongue blade device 400 includes a tongue contacting, or tong blade 401 having a distal end 402 for inserting into a patient's mouth during a surgical application and a proximal end 404 coupled to the spine 420. In this exemplary embodiment, hollow tube 406 is integrally formed with the tongue blade 400. In some embodiments, tube 406 rigidly connects the tongue blade 401 with the spine 180. The tongue blade 401 has a curved or rounded shape body 408 which acts as a tongue depressor and rests on the patient's tongue. The distal end 402 has a fork or U-shaped appearance formed by two protrusions 410, 412 extending therefrom and curved upwardly which form a channel or opening 416 therebetween. The hollow tube 406 extends from the elongated spine 418. The suction tube 406 has an opening 420 located adjacent to the proximal end 404 of the blade for removing noxious fumes, smoke, vaporized tissue, plumes generated by electrocautery and other debris from a patient's mouth during use in surgery. The hollow tube 406 connects the first portion to the spine 418 and provides a rigid support between the two. The use of the term rigid allows some flexing but only little to no minor deflection. In some embodiments, additional structure (not shown) connects the tongue blade 401 to the spine 180.

Along both sides of spine 418 are ratchet notches 290, similar to those described above with reference to FIGS. 2-3.

When in use, smoke, plumes generated by electrocautery, noxious fumes and vaporized tissue removal is effectuated by attaching connector end 422 of tube 406 to a pneumatic device typical of the art which causes a suction effect from the tongue blade.

While the surgical application is taking place, the spine 418 is held in the patient's mouth directing the suction tube 106 in the patient's mouth and removing smoke, fumes, plumes generated by electrocautery, and vaporized tissue via opening 420. Meanwhile, the first portion of the tongue blade 400, which is connected to the tube, is in the patient's mouth controlling the patient's tongue, thus preventing it from obstructing the application and removing smoke and vaporized tissue at the same time. The tongue blade suction tube 406 meanwhile evacuates the smoke, fumes, plumes generated by electrocautery, and vaporized tissue by sucking it through the receiving port or opening 420, through tube 406, and out through any known device the pneumatic or other suction causing device (not shown), attached to the tube barb 422.

Figure 5:
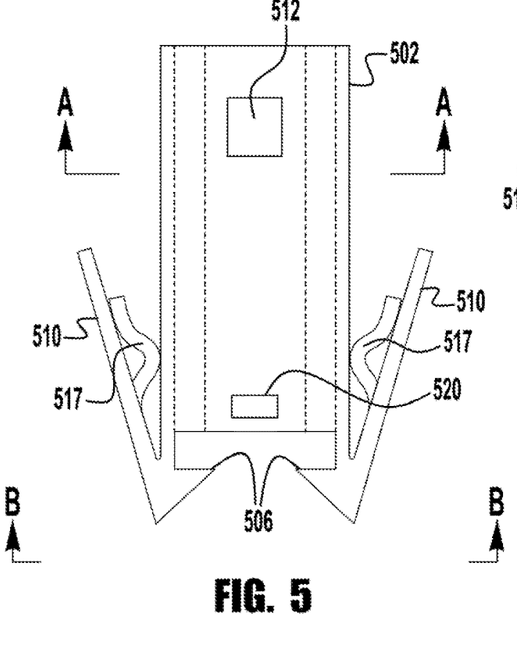
FIG. 5 is an exemplary embodiment of a ratchet mechanism for engaging the ratchet notches on the sides of the spine.
Figure 6:
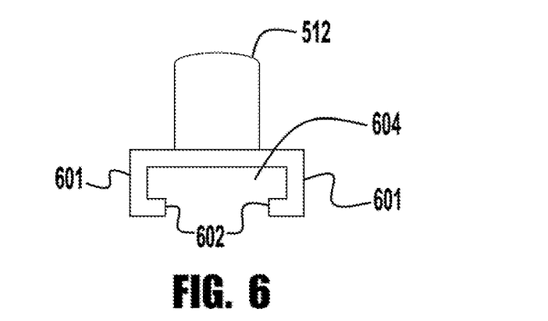
FIG. 6 is a cross-section of the ratchet mechanism of FIG. 5.
Figure 7:
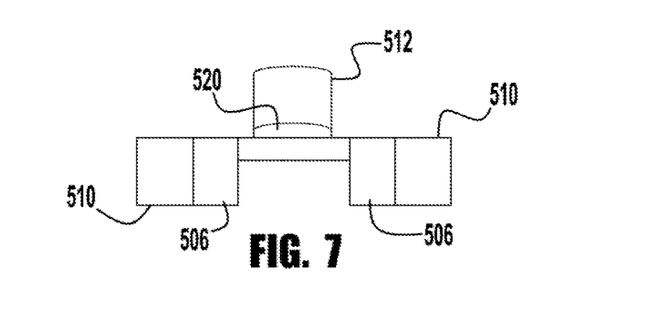
FIG. 7 is a cross-section of the ratchet mechanism of FIG. 5.

FIG. 5 is a plan view of an exemplary ratcheting mechanism 500. FIG. 6 is a cross sectional view taken at section "A" "A" and FIG. 7 is a front view taken at vantage points "B" "B". In some exemplary embodiments, ratcheting mechanism 500 is made of a plastic, one or more polymers, a high impact plastic, thermoplastic, or the like. In some embodiments, the one-piece unit which is fabricated from one or more metals, a composite, or the like. In some embodiments, the ratcheting mechanism 500 is made of a single molded piece. In some embodiments, the ratcheting mechanism 500 is printed with a three-dimensional printer. In some exemplary embodiments, ratcheting mechanism 500 is disposable. Exemplary ratcheting mechanism 500 is a "c" channel and has legs 601 and projections 602. The c-channel shape is configured to fit over the spine of a tongue blade, such as, for example, spine 272, or 418. Ratcheting mechanism 500 includes a connector 520 for connecting to an apparatus, such as, for example, rail 102 shown in FIG. 1. In addition, in some exemplary embodiments, ratcheting mechanism 500 includes a projection 512 that may be used by the surgeon to push ratcheting mechanism 500 upward. In some embodiments, projection 512 has a curved configuration that engages a user's thumb for movement of ratcheting mechanism 500. Integratedly molded into ratcheting mechanism 500 are ratchet teeth 506 and release arms 510. In some embodiments, an additional biasing member 517 that urges release arms 510 outward enduring ratchet teeth 506 securely hold ratcheting mechanism 500 in place. Pressing release arms 510 inward toward the body of ratcheting mechanism 500 causes ratchet teeth 506 to flex outward and disengage with ratchet notches 290 to allow movement of the ratcheting mechanism 500 with respect to the spine of the tongue blade.

Figure 5A:
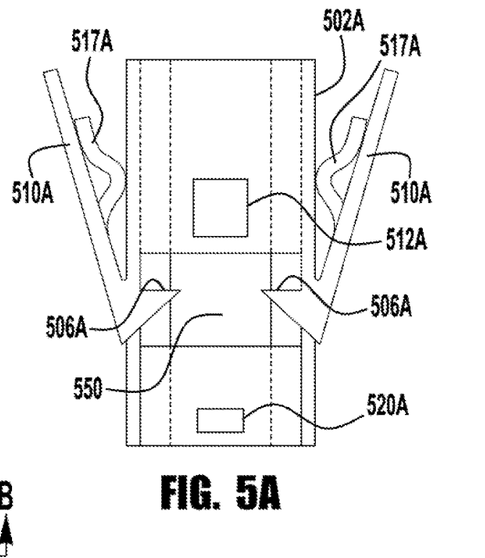
FIG. 5A is another exemplary embodiment of a ratchet mechanism for engaging the ratchet notches on the sides of the spine.

FIG. 5A is a plan view of an exemplary ratcheting mechanism 500A. Ratcheting mechanism 500A is similar to ratcheting mechanism 500 and like parts are numbered with the suffix "A". Ratcheting mechanism 500A has ratchet teeth 506A and release arms 510A located more centrally than ratcheting mechanism 500. Ratchet mechanism 500A includes an opening 550 in the c-channel 502A and ratchet teeth 506A move in and out of opening 550. Accordingly, it should be understood that ratchet teeth 506A and release arms 510A may be located anywhere along ratcheting mechanisms 500, 500A without deviating from the spirit and scope of the invention.

Figures 8, 9:
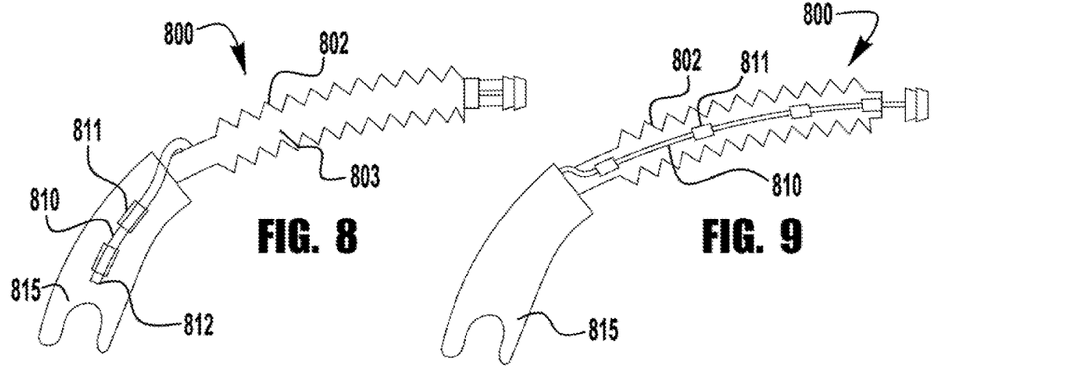
FIG. 8 is another exemplary embodiment of a tongue blade with ratchet notches along the side of the spine.
FIG. 9 is another exemplary embodiment of a tongue blade with ratchet notches along the side of the spine.
Figures 10, 11, 12:
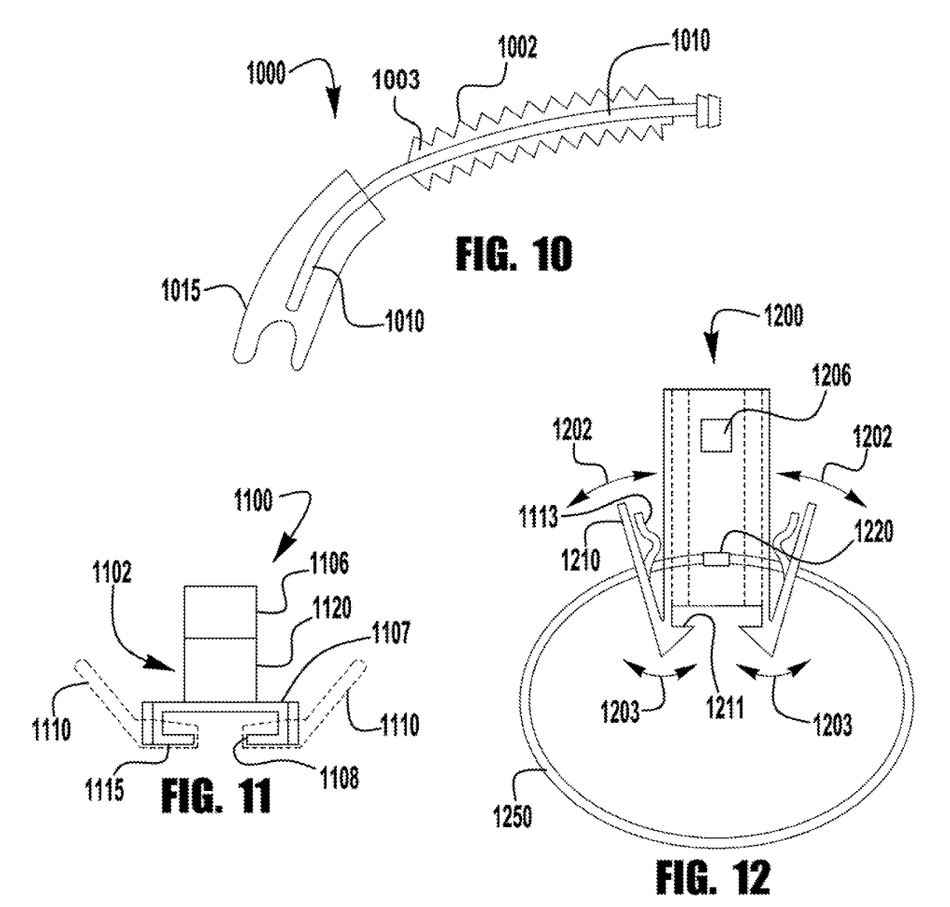
FIG. 10 is another exemplary embodiment of a tongue blade with ratchet notches along the side of the spine.
FIG. 11 is another exemplary embodiment of a ratcheting mechanism.
FIG. 12 is a cross-section of the exemplary embodiment of a ratcheting mechanism of FIG. 10.

FIGS. 8 and 9 illustrate another exemplary embodiment of a tongue blade device with ratchet notches on the spine and tubing retaining members. FIGS. 8-10 are more schematically illustrated and actually appear more like the tongue blades described above. FIG. 8 is a top view of a tongue blade 800 and FIG. 9 is a bottom view of tongue blade 800. Tongue blade device 800 includes a plurality of ratchet notches 802 along spine 803. The spine 803 is attached to tongue blade 815. A disposable tube 810 extends from connector 811 to end 812. A plurality of tube retaining members 811 extend along the front of spine 803 and the top of tongue blade 815 for retaining replicable tube 810. FIG. 10 illustrate another exemplary embodiment of a tongue blade device 1000 with ratchet notches 1002 on the spine and with integrated suction tube 1010 that connects the spine 803 to the tongue blade 1015. In some embodiments, the exemplary tongue blade devices above are fabricated from a plastic, one or more polymers, a high impact plastic, thermoplastic, or the like, one or more metals, a composite or the like. In some embodiments, the on-piece unit is formed on a three-dimensional printer.

FIGS. 11 and 12 are exemplary embodiments of ratchet mechanisms 1100, 1200. Ratcheting mechanism 1100 includes a c-channel 1107 having legs 1115 for retaining a tongue blade device (not shown). Ratchet mechanism 1100 includes lever arms 1110 for moving ratchet teeth 1108 inward and outward. In some embodiments, a biasing member causes the ratchet teeth 1108 to be biased inwards to engage ratchet notches in a tongue blade device not shown. In some embodiments, the material making up the lever arms 1110 and/or ratchet teeth 1108 cause the ratchet teeth 1108 to be biased inward. In some embodiments lever arms 1110 and ratchet teeth 1108 are formed as part of c-channel 1107. In some embodiments lever arms 1110 and ratchet teeth 1108 are formed separately from c-channel 1107 and are mechanically fastened thereto. Ratchet mechanism 1100 includes a rail connector 1120 for connecting to a rail (not shown, similar to rail 102 and rail 1250). Ratchet mechanism 1100 also includes a lever 1106 for engaging with the user's hand for moving ratchet mechanism 1100. In some embodiments, the exemplary ratchet mechanism 1100 is fabricated from a plastic, one or more polymers, a high impact plastic, thermoplastic, or the like, one or more metals, a composite or the like. In some embodiments, the on-piece unit is formed on a three-dimensional printer.

Ratcheting mechanism 1200 includes levers 1210, teeth 1211, thumb grip 1206, rail connector 1220 and rail 1250. Rail 1250 may be similar to rail 102. Rail 1250 engages the teeth or upper jaw when in use and provides counter traction with suction blade/tongue blade (not shown) which engage the tongue or lower jaw. Lever arm 1210 is movable in direction 1202 to move ratchet teeth in direction 1203. A biasing member 1213 biases lever arm 1210 outward and ratchet teeth 1203 inward to engage the ratchet teeth (not shown) of a tongue blade devce (not shown). In some embodiments, the exemplary ratchet mechanism 1200 is fabricated from a plastic, one or more polymers, a high impact plastic, thermoplastic, or the like, one or more metals, a composite or the like. In some embodiments, the on-piece unit is formed on a three-dimensional printer.

While the present invention has been illustrated by the description of embodiments thereof and while the embodiments have been described in considerable detail, it is not the intention of the applicant to restrict or in any way limit the scope of the appended claims to such detail. Additional advantages and modifications will readily appear to those skilled in the art. Therefore, the invention, in its broader aspects, is not limited to the specific details, the representative apparatus and illustrative examples shown and described. Accordingly, departures may be made from such details without departing from the spirit or scope of the applicant's general inventive concept.

I claim:

1. A mouth gag comprising:
   a tongue blade having a spine and an engagement portion for engaging a tongue of a patient;
   wherein the spine has a front surface, a back surface, a first side extending from the front surface to the back surface and a second side extending from the front surface to the back surface;
      a plurality of ratchet notches located along the first side; and
   a ratchet mechanism;
      the ratchet mechanism having one or more ratchet teeth for engaging the ratchet notches; and one or more release tabs for disengaging the one or more ratchet teeth from the ratchet notches.

2. The mouth gag of claim 1 further comprising a plurality of ratchet notches located on the second side.

3. The mouth gag of claim 1 wherein the ratchet notches have a first portion that is substantially perpendicular to the first or second side of the spine.

4. The mouth gag of claim 1 wherein the ratchet notches have a first portion that is substantially non-perpendicular to the first or second side of the spine.

5. The mouth gag of claim 1 wherein the ratchet mechanism is made from one of a plastic, a thermoplastic, and a polymer.

6. The mouth gag of claim 1 wherein the ratchet mechanism is molded in one unitary piece.

7. The mouth gag of claim 1 wherein the ratchet mechanism may be moved in a first direction along the spine without manually moving the release tabs and does not move along the spine in an opposite direction without moving the release tabs.

8. The mouth gag of claim 1 wherein the ratchet mechanism slides along the spine without a user squeezing the release tabs in a direction that is toward the portion of the tongue blade that contacts a person's tongue.

9. The mouth gag of claim 1 wherein the ratchet mechanism includes one ratchet tooth on each side of the ratchet mechanism.

10. The mouth gag of claim 1 further comprising a rail portion secured to the ratcheting mechanism.

11. The mouth gag of claim 1 wherein the ratchet mechanism includes more than one tooth on each side of the ratchet mechanism.

12. The mouth gag of claim 1 wherein a body portion of the ratchet mechanism is a "c" channel.

13. A ratchet mechanism for connecting to a tongue blade comprising;
 a body having a channel for enclosing a portion of a spine of a tongue blade device;
 the body having an opening along a back surface;
 the body having a rail connector and a handle on a front surface; and
 the body having a release lever and one or more ratchet teeth located on a first side surface that extends from the back surface to the front surface.

14. The ratchet mechanism of claim 13 further comprising a second release lever and one or more second ratchet teeth on a second side that extends from the back surface to the front surface.

15. The ratchet mechanism of claim 13 further comprising a rail.

16. A tongue blade device for connecting to a ratchet mechanism comprising;
 a spine; and
 an engagement portion for engaging a tongue of a patient;
 wherein the spine has a front surface, a back surface, a first side that extends between the front surface and the back surface; and a second side;
 a plurality of ratchet notches located along the first side;
 wherein the engagement portion extends outward from the back surface.

17. The tongue blade of claim 16 further comprising a plurality of ratchet notches located along the second side.

18. The tongue blade of claim 17 wherein the tongue blade is made of a polymer.

19. The tongue blade of claim 17 wherein the tongue blade is made of a polymer and is made of a unitary part.

20. The tongue blade of claim 17 further comprising one or more connectors for connecting a disposable tube to the tongue blade.

* * * * *